United States Patent [19]

Lin et al.

[11] Patent Number: 4,948,256

[45] Date of Patent: Aug. 14, 1990

[54] OPTICAL FIBER TYPE COLORIMETER

[75] Inventors: Chin-Ru Lin; Yueh-Joy Dong; Jinn-Trong Wu, all of Hsin Chu Hsien, Taiwan

[73] Assignee: Industrial Technology Research Institute, Hsin Chu Hsien, Taiwan

[21] Appl. No.: 240,195

[22] Filed: Sep. 6, 1988

[51] Int. Cl.$^5$ ............................................. G01J 3/42
[52] U.S. Cl. ..................................... 356/328; 356/446
[58] Field of Search ................. 356/326, 328, 446, 448

[56] References Cited

U.S. PATENT DOCUMENTS

| | | | |
|---|---|---|---|
| 4,076,421 | 2/1978 | Kishner | 356/446 |
| 4,669,873 | 6/1987 | Wirz | 356/328 |
| 4,756,619 | 7/1988 | Gerlinger et al. | 356/328 |
| 4,802,763 | 2/1989 | Gerlinger et al. | 356/446 |

FOREIGN PATENT DOCUMENTS 3701721  8/1988  Fed. Rep. of Germany ...... 356/326

Primary Examiner—F. L. Evans
Attorney, Agent, or Firm—Cushman, Darby & Cushman

[57] ABSTRACT

This invention relates to a optical fiber type colorimeter, and in particularly it refers to a colorimeter which uses optical fibers to transmit light to sample or reference matter. Scattered light reflected from matter surface is received by a optical fiber and then transmitted to a grating which splits light into spectrum. An A/D converter is connected to the driver circuit to communicated signal to computer for analysis of chromatic value, and determination of chrominace of sample, especially for analysis of some solid, products like textile, paper or brick. Since optical fibers are used in this invention, it enables more flexible installation of this invention. Moreover, precision of measurement is no longer affected by testing environment. The fabrication cost is lowered without the use of conventional reflective mirror.

5 Claims, 1 Drawing Sheet

OPTICAL FIBER TYPE COLORIMETER

BACKGROUND OF THE INVENTION

The ordinarily used instrument for measuring color is a spectrophotometer. The variation of light intensity must be calibrated before a sample is measured to ensure that precise data will be obtained. This method wastes a lot of time and the chrominance of sample measured is not too accurate. Moreover, greater error may be caused due to user's operation, a light source or a fiber loss in transmission.

To overcome the above drawbacks, applicant has designed a colorimeter to replace the ordinarily used one. This invention, an optical fiber type colorimeter, is a colorimeter for measurement of color of matter, and in particular for the measurement of the color of a solid product like textile, paper or brick.

SUMMARY OF THE INVENTION

This invention is mainly composed of a light source, a shade, several lenses, two optical fibers, a single slit, a grating, a detector array, a multiplexer, a driver circuit, an A/D converter and a computer.

The primary object of this invention is to measure the chrominance of a reference sample (e.g. a standard chromatic card) in a testing environment, and the result is used as a reference data which is compared with the chrominance of sample which is measured during a subsequent procedure. This invention is characterized in that it can eliminate the effect of variation due to light sources or fiber loss in transmission.

Another object of this invention is that its optical system consists of lenses, and in comparison, it is more compact than the conventional optical system which consists of reflective mirrors or integrating spheres.

Yet another object of this invention is that its fabrication cost is reduced because of the usage of lenses instead of conventional reflective mirrors, the cost of such reflective mirrors and like elliptic mirrors or parabolic mirrors being overly expensive.

The further object of this invention is that the detector array is a PN junction photodetector with charged amplifier. Such a driver circuit includes a multiplexer and a high speed integrator for selecting elements of detector array, integrating, amplifying and sending out the light projected on it. An extra pulse wave is used to adjust the sensitivity of detector array, and to vary the integration time so as to match different light sources and matters.

Another object of this invention is that the A/D converter is connected to a driver circuit to receive signal from it and convert the signal to digital signal which is then communicated to computer for evaluation of chrominance value of sample or reference matter.

DETAILED DESCRIPTION

Figure 1:
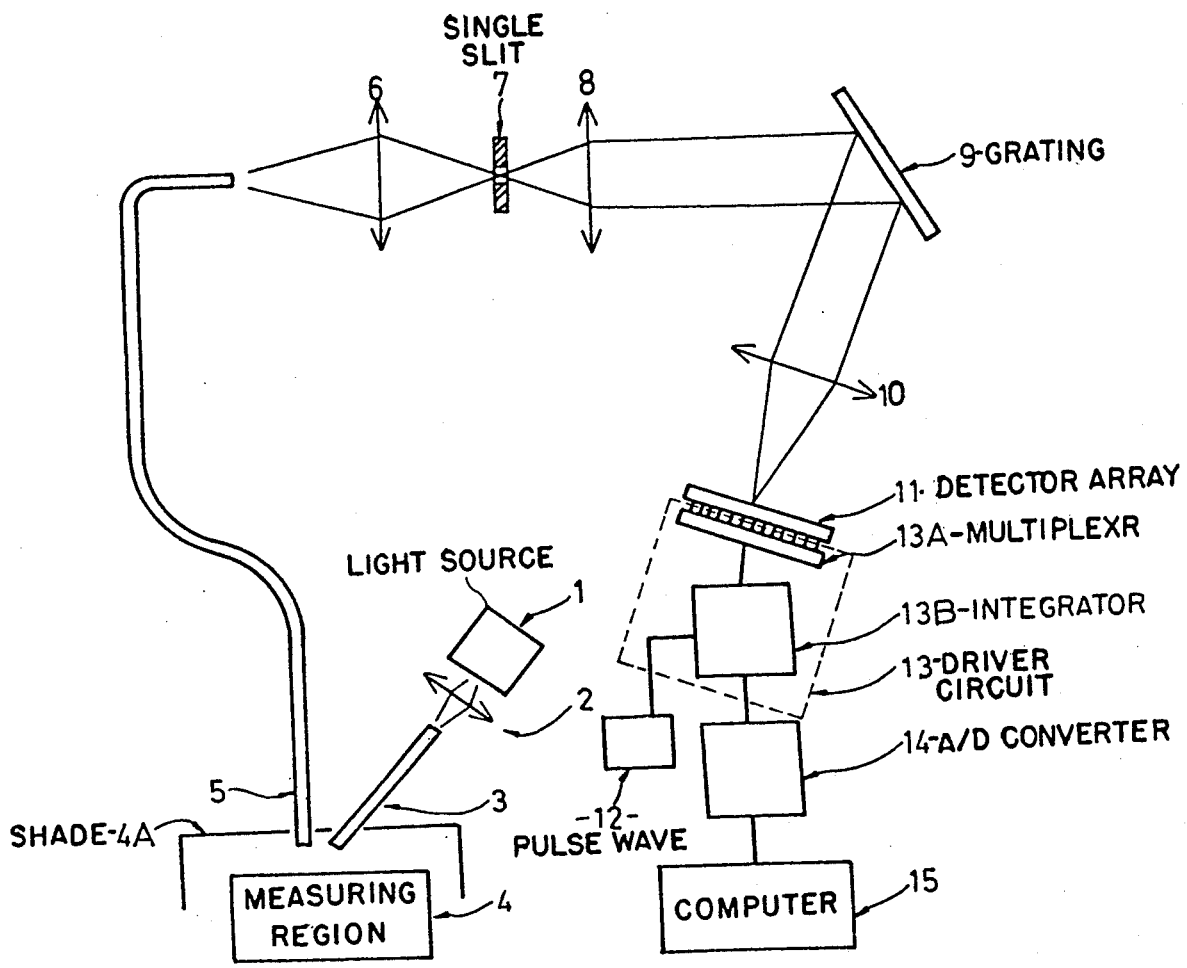
FIG. 1 is the schematic illustration of an embodiment of this invention.

FIG. 1 is the schematic illustration of an embodiment of this invention. This invention uses the 45°/0° illumination and reception method recommended by CIE (i.e. the light incident angle to sample or reference matter is 45°, where receiver of the reflective light locates at position perpendicular to sample or reference matter) to measure the chrominance value of sample (or reference matter). Light source 1 transmits a light beam to an optical fiber 3 through lens 2. In order to eliminate the effect of variation of surroundings to the precision of this invention, a shade 4A is fitted in measuring region 4 for shielding of external light. Optical fiber 3 projects light to sample surface at an incident angle of 45°, where optical fiber 5 receives perpendicularly scattered light from sample and then transmits light beam to spectral system in rear side.

The light from end of optical fiber 5 is projected to the single slit 7 after being directed thereto by lens 6. A lens 8 is installed behind the single slit 7. At grating 9, the light beam is split into a spectrum which is focused to detector array 11 by lens 10. Such detector array 11 is a PN junction photodetector with charged amplifier, where basically, it can have 35 elements. Its driver circuit 13 includes a multiplexer 13A and a high speed integrator 13B, which can select elements of array, and integrate, and amplify, and then send out the signal falling on array, like the Hamamatsu C2334-35Q circuit. Since this invention uses a pulse wave 12 to adjust the sensitivity of the detector array, it can vary the integration time so as to match different matters and light sources.

Signal from multiplexer 13A is transmitted to computer 15 through an A/D (analog/digit) converter 14. Then, from CIE tristimulus color valve or CIE L*, a*, b* cube root color coordinates, the chromatic value of sample can be evaluated.

The grating used in this invention is holographic grating which can provide good dispersion and project image of different wavelengths on single slit to detector array 11, replacing the mechanical scanning of a conventional spectrometer.

The sample's chrominance is determined by spectral reflectance factor $\beta(\lambda)$ which is defined as $$\beta(\lambda) = \frac{\Phi_\lambda (\omega) d\lambda}{\Phi_{o\lambda} (\omega) d\lambda} \qquad (1)$$

where $\Phi_\lambda (\omega)$ is the flux of light received at a side angle to the surface of the sample, and $\Phi_{o\lambda} (\omega)$ is the flux of light received at an solid angle to the 15 surface of reference matter.

Obviously, from equation 1, chrominance, differences due to differences in light sources, optical fibers and lenses used in this invention are cancelled.

This colorimeter is designed mainly for textile, paper or brick. Chromaticity of liquid sample like paint, dye and so on can also be measured with the usage of suitable peripheral facilities and containers.

This invention gives a correct chromatic value by comparison, and therefore it is no longer effected by variation of surroundings, instrumental errors, or user's operation error. A standard chromatic card is input to computer, and the chrominance of sample in the same environment is then input for comparison to give a objective chromatic value.

In conclusion, this invention uses optical fibers to transmit light, and utilizes lenses instead of reflective mirror. It not only enables accurate analysis of chromacity, but also largely reduces the fabrication cost. In fact, this invention is very practical.

We claim:
1. An optical fiber colorimeter comprising:
a light source for generating a light beam;
a first optical fiber;

a first lens interposed between said light source and said first optical fiber, said first optical fiber and said first lens positioned so as to direct said light beam into said fiber;

a sample placed at a 45° angle from an exit end of said first optical fiber so as to have said light beam incident on a surface thereof;

a shade for defining a measuring region around said sample;

a second optical fiber perpendicular to the sample, positioned so as to receive light scattered from the surface;

a second lens interposed between an exit end of said second optical fiber and a front side of a single slit;

a diffraction grating;

a third lens positioned after a backside of said single slit for directing light passing through said slit toward said diffraction grating;

a detector array;

a fourth lens for focusing light diffracted by said grating onto said detector array which converts a spectrum from the grating to electronic signals;

a driver circuit including a multiplexer and a high speed integrator; and an analog/digital (A/D) converter connecting said driver circuit to a computer which analyzes the electronic signals;

said optical fiber colorimeter able to measure a chrominance of the sample and a value obtained is used as a reference standard, to be stored in the computer, which will be used for later comparisons thereby making it unnecessary to consider chromatic differences due to surroundings.

2. Apparatus as claimed in claim 1, wherein the optical fiber colorimeter is compact due to use of the first through fourth lenses.

3. Apparatus as claimed in claim 1, wherein the optical fiber colorimeter is flexible in layout due to the use of the first and second optical fibers.

4. Apparatus as claimed in claim 1 wherein the detector array includes a pn junction photodetector with a charged amplifier, and the driver circuit are used in conjunction with one another so as to select elements of the detector array, and integrate, amplify and send out signals projected thereon with an extra pulse wave being added for adjusting the sensitivity of the detector array and varying integration time so as to correlate different light sources and matters.

5. Apparatus as claimed in claim 1 wherein the diffraction grating is a holographic grating.

* * * * *